United States Patent [19]

Anderson et al.

[11] Patent Number: 5,334,839
[45] Date of Patent: Aug. 2, 1994

[54] POSITION SENSITIVE RADIATION DETECTOR

[75] Inventors: Jon A. Anderson, Plano; Peter P. Antich, Richmond, both of Tex.

[73] Assignee: The Board of Regents, The University of Texas System., Austin, Tex.

[21] Appl. No.: 38,677

[22] Filed: Mar. 26, 1993

Related U.S. Application Data

[63] Continuation-in-part of Ser. No. 784,593, Oct. 29, 1991, Pat. No. 5,281,821.

[51] Int. Cl.$^5$ .............................................. G01T 1/20
[52] U.S. Cl. .................................... 250/368; 250/367; 250/366
[58] Field of Search ........................ 250/368, 367, 366

[56] References Cited

U.S. PATENT DOCUMENTS

| | | |
|---|---|---|
| 3,978,337 | 8/1976 | Nickles et al. . |
| 4,677,299 | 6/1987 | Wong .................................. 250/363 |
| 4,749,863 | 6/1988 | Casey et al. . |
| 4,788,436 | 11/1988 | Koechner ........................ 250/483.1 |
| 4,823,016 | 4/1989 | Yamashita et al. . |
| 4,829,185 | 5/1989 | Cerff . |
| 4,942,302 | 7/1990 | Koechner . |
| 4,973,845 | 11/1990 | Mastrippolito . |
| 4,983,841 | 1/1991 | Stewart . |
| 5,103,098 | 4/1992 | Fenyves ............................. 250/368 |
| 5,103,099 | 4/1992 | Bourdinand . |
| 5,150,394 | 9/1992 | Karellas . |
| 5,281,821 | 1/1994 | Antich et al. ....................... 250/367 |

FOREIGN PATENT DOCUMENTS

| | | |
|---|---|---|
| 57-76466 | 5/1982 | Japan . |
| 60-159675 | 8/1985 | Japan . |
| WO85/04959 | 11/1985 | PCT Int'l Appl. ................. 250/367 |

OTHER PUBLICATIONS

Antich et al, "Development of a High Resolution Scintillating Fiber Gamma Ray Telescope," Nucl. Instr. and Methods, A297:514–520 (1990).
Antich et al, "Development of a High Resolution Scintillating Fiber Gamma Ray Telescope," IEEE Transactions on Nuclear Science, 38(2):568–573 (1991).
Atac et al, "High Resolution Scintillating Fiber Gamma Ray Detectors for Medical Imaging," Abstracts, IEEE Joint Nuclear Science Symposium and Medical Imaging Conference, No. 5M9, 38 (1990).
Chaney et al, "Simulation of Scintillating Fiber Gamma Ray Detectors for Medical Imaging," Abstracts, IEEE Joint Nuclear Science Symposium and Medical Imaging Conference, No. 5M8, 38 (1990).
Singh, "An Electrically Collimated Gamma Camera for Single Photon Emission Comuted Tomography. Part I: Theoretical Considerations and Design Criteria," Med. Phys., 10(4):421–435 (1983).
Uchida et al, "Design of a Mosaic BGO Detector System for Positron CT," IEEE Transactions on Nuclear Science, 33(1):464–467 (1986).

(List continued on next page.)

Primary Examiner—Paul M. Dzierzynski
Assistant Examiner—Drew A. Dunn
Attorney, Agent, or Firm—Arnold, White & Durkee

[57] ABSTRACT

An apparatus and method are disclosed for detecting and locating the origin of a gamma ray in a medical diagnostic imaging system. At least one primary fiber, which is a scintillating optical fiber, is positioned to receive radiation from a gamma ray source. At least one secondary fiber intersects the primary fiber at a non-zero angle. Both fibers have a core surrounded by a cladding, with the claddings of the two fibers in optical contact at an intersection point. Both the primary and secondary fibers are provided with means for detecting light propagated in the fibers. The interaction of radiation such as a gamma ray with the primary fiber will result in the propagation of light in both the primary and secondary fibers, thereby permitting the determination of the site of impact of the gamma ray in the detector, and possibly also enabling the determination of the path of incidence of the gamma ray.

11 Claims, 5 Drawing Sheets

OTHER PUBLICATIONS

Chaney, "Monte Carlo Simulation of Gamma Ray Detectors Using Scintillation Fibers," SPIE 1159:18–26 (1989).

Atac et al, "High Resolution Gamma-Ray Telescopes and Medical Imagers Using Scintillating Fibers and Position Sensitive Photomultipliers," SPIE 1161:178–188 (1989).

Atac et al, "High Resolution Gamma Ray Telescope Using Scintillating Fibers and Position Sensitive Photomultipliers," Nuclear Physics B (Proc. Suppl.) 10B:139–142 (1989).

Atac et al, "A High Resolution Scintillating Fiber Gamma-Ray Telescope," Proc. First International Symposium on the Super Collider, 699–707 (Feb. 1989).

Fenyves et al, "Space-Based High Resolution Gamma-Ray Telescope," SPIE 879:29–36 (1988).

Petroff et al., "High Energy Particle Tracking Using Scintillating Fibers and Solid State Photomultipliers," IEEE Transactions on Nuclear Science, 36(1):163–164 (1989).

Buchsbaum et al, "Functional and Anatomical Brain Imaging: Impact on Schizophrenia Research," Schizophrenia Bulletin, 13(1):115–132 (1987).

Lancaster et al, "Computers, Physics and Medicine: Imaging the Body," Computers and Physics, 16–22 (Sep.–Oct. 1988).

Langham, "PET Scanning: Earlier and Better Pictures of Disease," Texas Times, 43–45 (1985).

Andreasen, "Brain Imaging: Applications in Psychiatry," Science, 239:1381–1388 (1988).

Brownell et al, "Positron Tomography and Nuclear Magnetic Resonance Imaging," Science, 215:619–626 (1982).

Blumbenfeld et al, "Plastic Fibers in High Energy Physics," 603–606 (Elsevier Science Publishers).

Ghosh, "Current Applications of Computers in Nuclear Medicine," J. Nuclear Medicine 31(2):20A–28A (1990).

Atac et al, "High Resolution Scintillating Fiber Gamma Ray Detectors for Medical Imaging," 1990 IEEE Nuclear Science Symposium Conference Record, 2:1128–1130 (Oct. 1990).

POSITION SENSITIVE RADIATION DETECTOR

This application is a continuation-in-part of U.S. Ser. No. 784,593, filed on Oct. 29, 1991, now U.S. Pat. No. 5,281,821, which is incorporated in this application by reference.

BACKGROUND OF THE INVENTION

This invention relates to an improved method and apparatus for locating the origin of radiation, such as a gamma ray, in an imaging system. In particular, this invention relates to a method and apparatus for determining the origin of a gamma ray as part of a technique of imaging internal organs in a living subject.

There are many situations in medicine where it is desirable to obtain images of a patient's internal organs or body functions. The imaging technology that is used to do this includes a variety of techniques such as magnetic resonance imaging (MRI), computed tomography (CT), single photon emission computed tomography (SPECT), and positron emission tomography (PET).

Generally speaking, in PET, a radionuclide is administered internally to a living subject. A positron from the decaying radionuclide encounters and annihilates with an electron, resulting in a pair of 511 keV annihilation photons which are emitted in exactly opposite (180°) directions from the annihilation site in the subject. By arranging banks of radiation detectors—typically scintillation detectors—all around the subject, the origin of the gamma ray can be determined. Substantially simultaneous detection of photons in opposingly situated detectors defines the site of the positronelectron annihilation as lying somewhere along a line directly between the opposing detectors. Typical PET scanners or tomographs include complex computerized data systems for collecting the information obtained and using it to reconstruct an image of the target organ, using mathematical techniques similar to those employed in computerized tomography.

The radioactive isotopes used in PET include, but are not limited to, $^{18}F$, which has a half-life of approximately 110 minutes, $^{11}C$ (half-life of approximately 20 minutes), $^{13}N$ (half-life of approximately 10 minutes), and $^{15}O$ (half-life of approximately 2 minutes). Because of the relatively short half-lives of the radioisotopes used, they are typically produced in an on-site cyclotron or other particle accelerator. Other nuclides exist which have either a long half life or a parent with long half life. These can be used without on-site cyclotrons, but they have generally less desirable chemical or physical characteristics. The practical need for an on-site cyclotron dramatically increases the cost of PET and therefore has limited the number of such systems in place.

In contrast, in SPECT, a single photon is emitted from a radionuclide at a site in the patient's body. The photon is again detected, but in contrast to PET, the origin of the photon is determined by analyzing the information obtained when the single photon strikes different portions of an array of radiation detecting elements, thereby permitting the deduction of its path. SPECT uses longer-lived isotopes than PET, including but not limited to $^{99m}Tc$ (half-life of approximately 6 hours) and $^{201}Tl$ (half-life of approximately 74 hours). However, the resolution obtainable through SPECT imaging is lower than that presently available in PET systems.

In both prior art PET and SPECT systems, the scintillating detectors are able to detect the emitted photons (also called gammas) by means of a phenomenon whereby a photon interacts with an atom of the scintillating detector, which may be in the form of a scintillating optical fiber. This interaction results in the ejection of a so-called photoelectron or Compton electron. The ejected electron transfers energy to atomic, molecular, or crystalline structures in the fiber, and causes the emission of light quanta. The light propagates toward an end of the fiber, where it is detected by means such as photomultipliers. The ejected electron, meanwhile, will sometimes have sufficient energy to move on and interact with at least one more scintillating fiber in an array of alternating x-y planes of orthogonal fibers, again resulting in the generation of light in those fibers. By detecting the light generated in the two or more fibers, and then determining the point at which those fibers intersect, one can determine the site of the event.

It is crucial for electronically collimated SPECT imaging that the path of the incoming gamma ray be determined. This is possible by detecting two (Compton) events within the same detector or two different detectors; the line through the two points at which the fibers intersect determines the direction of the incoming gamma ray.

Presently, both PET and SPECT systems employing optical fibers have less than optimal resolution and efficiency of detection of gamma rays. Two factors that reduce the efficiency of these systems are: (1) gammas (photons) which pass through the scintillating fiber array without generating a photoelectric or Compton event, and (2) events which go undetected due to the requirement that the electron traverse at least two layers of fibers in the z direction in order for detection to be accomplished. This poses a particular problem in SPECT systems at low energy. A fiber of for example 0.25 mm diameter will stop an electron of kinetic energy 150 keV; a fiber of 0.05 mm diameter stops electrons of 50 keV. Thus Compton interactions of a few hundred keV gamma rays most frequently excite only one fiber in prior art radiation detecting systems. In such a situation, the position of the origin of the gamma ray is not detectable without using extremely fine fibers, which are both inherently inefficient and expensive.

There is a need for improved imaging methods and apparatus that would eliminate or reduce the shortcomings of the prior art, not only in PET and SPECT, but also in other imaging technologies.

SUMMARY OF THE INVENTION

The present invention relates to apparatus for detecting and locating the origin of radiation, such as a gamma ray, which may be used in a medical diagnostic imaging system, or in imaging systems for other applications. Such apparatus includes at least one primary optical fiber which has a core surrounded by cladding, with the primary fiber being positioned to receive radiation from a radiation source, and at least one secondary optical fiber which intersects the primary fiber at a non-zero angle and which has a core surrounded by cladding, and whose cladding is in optical contact with the cladding of the primary fiber. The apparatus also includes a plurality of means for detecting light which are coupled to the primary fiber and the secondary fiber, and means for collecting and processing data from the means for detecting light, to locate the origin of the radiation. The core of both the primary fiber and the secondary fiber may or may not have waveshifter incorporated in them, but the cladding of either or both of the primary fiber and the secondary fiber have at least one waveshifter incorporated in them. Wave shifter is incorporated in the core of scintillating fibers to shift the primary scintillation light, which is normally in the ultraviolet, to a longer wavelength which can be efficiently detected by a photomultiplier or photodiode and which will be transmitted through the fiber with less attenuation. The core of at least one of the primary fiber and the secondary fiber is scintillating.

The apparatus preferably includes a plurality of primary fibers and a plurality of secondary fibers, with the primary fibers being arranged substantially parallel to each other in a first plane. Likewise, it is preferred that the secondary fibers be arranged substantially parallel to each other in a second plane which is parallel and adjacent to the first plane. In an especially preferred embodiment, the primary fibers are orthogonal to the secondary fibers. Furthermore, in a preferred embodiment, the two sets of fibers can both act as either a primary or a secondary fiber depending on the site at which the gamma ray initially interacts.

The present invention also relates to a method for detecting and locating the origin of radiation, such as a gamma ray, in a patient as part of a medical diagnostic imaging system. Such a method includes the steps of (1) emitting radiation, such as a gamma ray, from a radiation source in a patient's body; (2) ejecting an electron in the scintillating core of a primary optical fiber as a result of an interaction between the radiation and the scintillating core of the fiber, thereby causing the emission of light quanta in the primary fiber; (3) transferring a portion of the light quanta from the primary fiber to a secondary optical fiber which intersects the primary fiber at a non-zero angle and is in contact with the primary fiber; (4) detecting the light quanta from the primary fiber and the secondary fiber; and (5) determining the location of the interaction between the radiation and the primary fiber by identifying the location of the contact between the primary fiber and the secondary fiber. The transfer of a portion of the light quanta from the primary fiber to the secondary fiber in step (3) is accomplished by means of re-emission of the light quanta when they interact with cladding that surrounds the fibers. The cladding incorporates at least one waveshifter (while the scintillating core may or may not contain any waveshifter), resulting in waveshifting of the light when it is re-emitted. For electronically collimated SPECT, steps 2-5 must be repeated at least once.

In the present invention, an electron provided by a gamma ray interaction need only generate light in a single fiber, in contrast to the requirement of prior art systems that such an electron produce light in at least two fibers. A fraction of the light quanta which are generated by the electron travel to the two ends of the first fiber, and are detected there by photomultipliers. The remaining fraction, or a portion thereof, is transferred to an adjacent, preferably orthogonal fiber whose cladding is in contact with the cladding of the first fiber, and then travels to the two ends of that second fiber, where the light is again detected by photomultipliers. The substantially simultaneous signals produced by the photomultipliers for the two fibers, plus the known point of intersection (contact) of the two fibers, identifies the site where the radiation struck the fibers, and thus permits determination of the location of the source of the radiation. This scheme is referred to as "conference sensing."

It should be noted that the accidental spill-over (crosstalk) of the light field from one fiber to adjacent ones is an unwanted effect in general. Conference sensing refers to the enhanced and controlled transfer of light from one fiber to a second one crossing it, and to the suppression of the "crosstalk."

The present invention can be used in a variety of digital imaging applications such as computed tomography, positron emission tomography, single photon emission computed tomography, fluoroscopy, and X-ray digital imaging.

The present invention permits the use of larger fibers than are suitable in prior art scintillating fiber detection systems for the energies used in nuclear medicine. A system with such larger fibers has several advantages over prior art systems, including: (1) more ease in fabrication, since fewer fibers are needed to produce a detector of equivalent stopping power, (2) better signal-to-noise characteristics for the detector since the total energy of the Compton or photo-electron may be stopped in a single fiber (in a detector employing small fibers, the number of visible light photons generated in and transmitted by a single fiber may be on the order of the noise level for the fiber/photomultiplier combination), and (3) less unwanted cross-talk. These factors lead to (4) higher detector sensitivity and (5) better energy resolution, which in turn produce (6) greater system efficiency and (7) more accurate determination of the direction of the original gamma ray. The use of larger fibers also allows (8) a significant reduction (by a factor of about 35) in the complexity of the electronics and associated detector costs.

The present invention has the additional advantage that only light emitted in a relatively narrow cone in the primary fiber, having a half angle equal to a certain critical angle, can enter the cladding and subsequently be partially transferred to an adjacent secondary fiber; light emitted outside that cone will encounter total internal reflection and be trapped in the primary fiber. This increases the ability to localize the transfer of light quanta from a primary fiber to a secondary fiber to the site of the scintillation event itself. Further, because the cladding is intact on both primary and secondary fibers, there will be efficient propagation of the re-emitted photons that travel down both fibers. Other benefits of the present invention are explained in the following detailed description.

DETAILED DESCRIPTION OF SPECIFIC EMBODIMENTS

The present invention relates to position sensitive radiation detectors employing scintillating optical fibers in an optically coupled (conferencing or controlled cross-talk) configuration. In this general class of detector, which can be termed a distributed detector, the position of a radiation interaction within the volume of the detector is determined by observing essentially simultaneous light pulses in two scintillating optical fibers which cross at non-zero angles. The device works by coupling scintillation light originating in one fiber due to the interaction of radiation (gamma rays, fast electrons, beta particles, etc.) in that fiber into a second fiber. The coupling is such that significant light transfer occurs only near the intersection of the two fibers. Thus, observing essentially coincident light pulses from the two fibers indicates that a radiation interaction occurred near their intersection.

Figure 1:
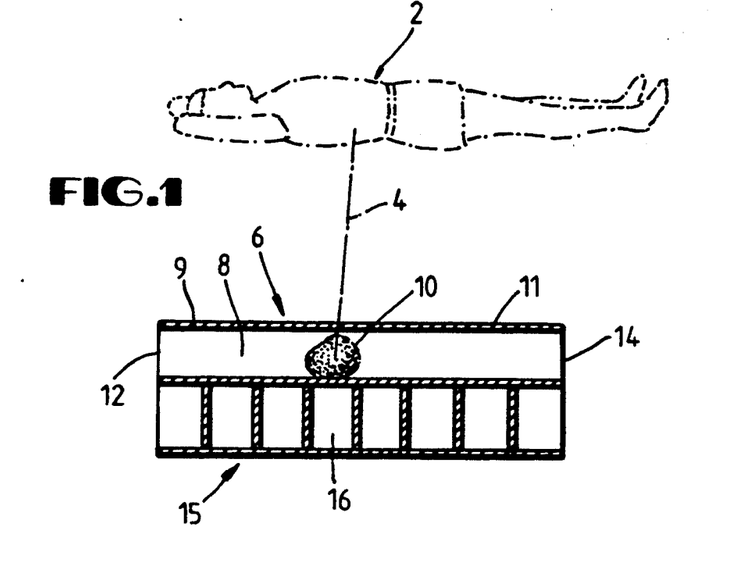
FIG. 1 shows the relationship of the living subject to a detector in accordance with the present invention.
Figure 2:
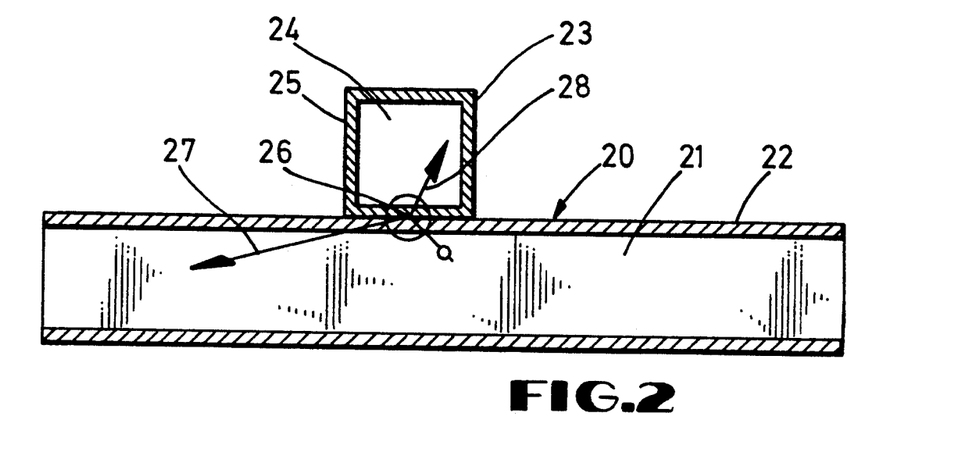
FIG. 2 shows two orthogonal optical fibers and the transfer of light quanta from one to the other.

FIGS. 1 and 2 illustrate the basic mechanism. As shown in FIG. 1, a photon produced by the decay of a radioisotope in the body 2 travels along a path 4 toward a detection apparatus 6, which includes a first scintillating optical fiber 8. The fiber 8 has a scintillating core 9 and a cladding 11. The photon interacts with an atom of the scintillating fiber core 9 at a point 10, ejecting an electron. The electron excites the fiber 8, thus losing its energy to the fiber. One result of this loss of energy is the emission of ultraviolet light; the number of quanta of light produced is proportional to the energy deposited by the electron along its path. If a waveshifter is present, the ultraviolet light will be converted to visible light photons which can propagate along the fiber 8 towards its two ends 12 and 14, where they are detected by photomultipliers (not shown in FIG. 1) at the ends of the fiber. Any event in which a sufficient number of quanta are detected activates the electronic equipment for analyzing and recording the event (not shown in FIG. 1).

Adjacent the first scintillating fiber 8 is an orthogonal array of optical fibers 15. This array of secondary fibers 15 may or may not be scintillating.

The transfer of a portion of the light quanta to a secondary fiber can be more clearly understood in FIG. 2. The primary fiber 20, with its scintillating core 21 and its cladding 22, is the site of the original scintillation event. The secondary fiber 23, with a core 24 and a cladding 25, is adjacent and orthogonal to the primary fiber 20. The claddings 22 and 25 are in optical contact.

The light (UV or near-UV) generated by the scintillation event interacts with the claddings 22 and 25 at point 26. Waveshifters are present in the claddings 22 and 25. The light is absorbed and re-emitted isotropically in the claddings 22 and 25. One fraction of the light 27 will travel down the primary fiber 20, in which the original scintillation light was generated. A second fraction 28 of the light will travel down the adjacent secondary fiber 23. The first and second fractions can then be detected by, e.g., photomultipliers attached to the fibers.

Figure 3:
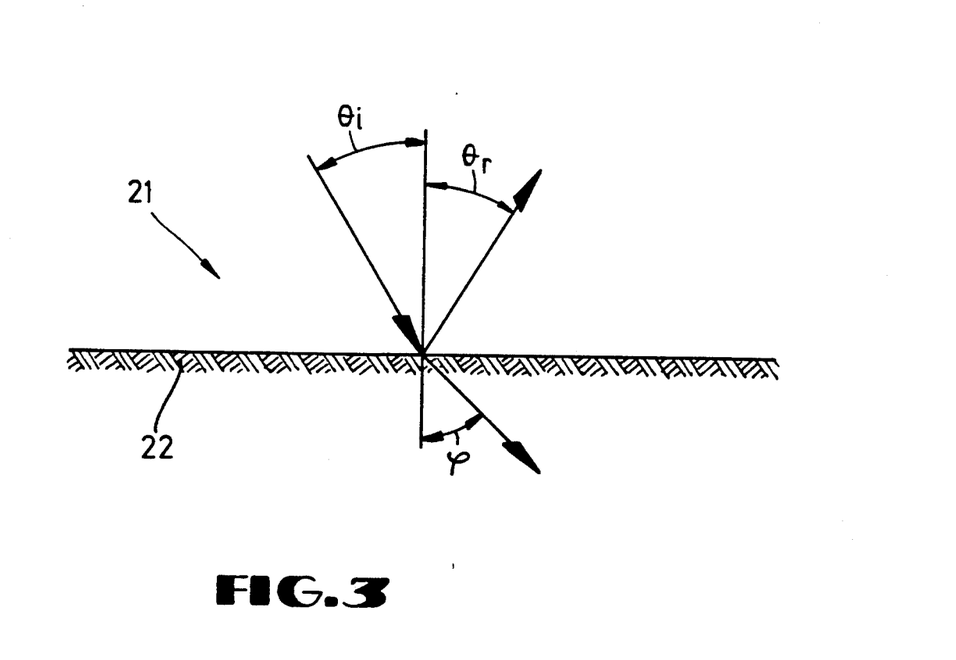
FIG. 3 shows the angle of incidence of light emitted in the core of a fiber as it strikes the fiber's cladding.

Scintillating optical fibers are typically made using a core of material having index of refraction $n_{core}$ and a thin cladding having index of refraction $n_{clad}$. This causes a phenomenon called total internal reflection (TIR) to occur whenever the angle of an incident light ray equals or exceeds the critical angle $\theta_c = \arcsin(n_{clad}/n_{core})$, as shown in FIG. 3. The light passing through the core 21 will strike the interface of the core 21 and the cladding 22 with an angle of incidence $\theta_i$ as shown in the figure. Rays originating in the core incident at the surface of the cladding at angles $\theta_i$ equal to or in excess of the critical angle $\theta_c$ will be totally reflected back into the core material. Rays which are incident on the core-cladding interface at less than the critical angle will have some probability for passing into the cladding; the size of the reflection coefficient is determined by the exact angle of incidence, the difference in refractive index between the core and the cladding, and the polarization of the incident light.

Thus, interaction in the fiber cladding is localized near the scintillation event by the nature of the fiber. Roughly equal amounts of light will be re-emitted into the original (primary) fiber and the crossing (secondary) fiber. This light can freely enter the core, since no TIR will occur for rays entering the core from the cladding. Finally, because the cladding is intact on both fibers, there will be efficient propagation of the re-emitted photons that travel down the fiber.

The quanta of light transferred to the secondary fiber travel in both directions toward the two ends of the second fiber, where photomultipliers (not shown in FIGS. 1 or 2) detect them in the same way as at the ends of the first fiber.

The near-simultaneous detection of light in the first fiber 8 and the secondary fiber 16, and the knowledge of the point of intersection and contact of those two fibers, permits the determination of the site of the radiation interaction, and thus the deduction of the origin of the gamma ray, using either mechanical or electric collimation. In the first case, a set of collimators separates the patient from the fibers; in the second, at least two interactions are detected in coincidence and the direction is computed.

Desirable characteristics for the coupling mechanism include the following. The optical coupling between the crossed fibers should be strong only in the region of the original radiation interaction. This localizes the interaction within the volume of the detector and will contribute to maximizing the spatial resolution of the detector system. Once light has been coupled into the second fiber, it should remain trapped in the fiber. Leakage back into other fibers will degrade the spatial resolution of the detector and may decrease the light intensity in the fiber to the point where optical noise in the fiber and electrical noise in the photo-detector interfere with operation of the detector. A significant fraction of the scintillation light should be coupled into the second fiber. This is again required in order to keep the light intensity in the second fiber high enough to permit detecting it above the noise sources in the system.

Figure 4:
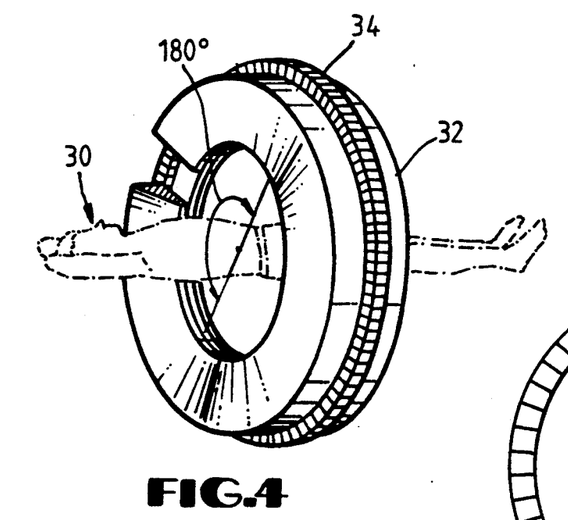
FIG. 4 shows a patient positioned in an imaging apparatus which can incorporate the present invention.

FIG. 4 shows an example of apparatus in accordance with the present invention. A patient 30 is positioned in a support ring 32. An appropriate radioisotope is administered to the patient 32. Stacks of scintillating fibers 34 can be positioned about the patient on the support ring 32.

Figure 5:
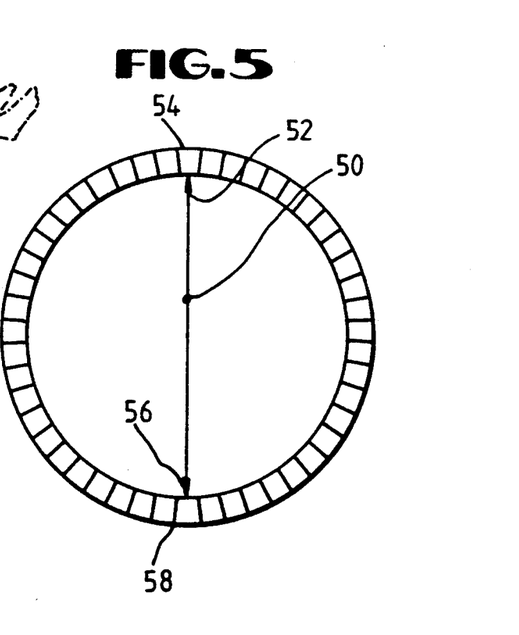
FIG. 5 shows a cross-sectional representation of a PET detector apparatus which can incorporate the present invention.

In a PET application, the radionuclide in the patient's body emits a positron which, after travelling a short distance from the nucleus, interacts with an electron. The resulting annihilation yields two photons having energy of 511 keV, and which move in exactly opposite directions. FIG. 5 illustrates the spatial origin 50 of the gamma ray, i.e., the position of the pair annihilation. One photon 52 strikes a part of the scintillating fiber stack 54 and the other photon 56 strikes the opposite portion 58 of the scintillating fiber stack. By determining the two points where the photons strike at substantially the same time, a line which passes through the point at which the photons originated can be calculated.

Suitable scintillating optical fibers can have diameters ranging from 0.01 mm to 5 mm or more. Suitable materials for such fibers include polystyrene doped with TP (p-terphenyl) or PPO (diphenyloxazole). The unshifted wavelength may be in the range 350–380 nm. Conventional fibers, incorporating an additional waveshifter in the body of a scintillatot, can be obtained from Optectron (France), Bicron Corporation (Newbury, Ohio), and Kuraray/Kyowa (Japan). The waveshifter moves the wavelength of the emitted light to a longer wavelength.

The scintillating optical fiber emits light when radiation in the form of gamma rays, neutrons, beta rays, fast electrons, positrons, etc., interact in the fiber material. This scintillation may be an intrinsic property of the fiber material or it may be enhanced by the addition of certain materials. The primary scintillation (light emission) usually occurs in the ultraviolet (UV) portion of the spectrum and is isotropic. The UV light may be strongly absorbed by the fiber material and also may not be efficiently detected by the photodetector. Waveshifters distributed in the fiber are used to convert the UV light to longer wavelengths in order to avoid any absorption problems and to match the spectral response of the photodetector. If plastic fibers are used to make the scintillating fiber, the waveshifter is typically an organic dye with its absorption peak in the UV and its emission peak in the visible region of the spectrum. Emission of light from the waveshifter is isotropic and does not depend on the direction of the incident primary scintillation light. Successive waveshifters may be used to convert the emitted light to even longer wavelengths. More than one waveshifter can be used in a single fiber. For example, one waveshifter might be used in the fiber core and a secondary waveshifter could be used in the cladding.

Waveshifters suitable for inclusion in either the core or the cladding include but are not limited to POPOP (diphenyloxazolyl-benzene) and TPB (tetraphenyl butadiene). Such chemicals are available from Sigma Chemical Company (St. Louis, Mo.) and other suppliers.

Waveshifters can also be used to prevent photons that are crossing over from a first optical fiber to a second optical fiber from crossing back over into the first optical fiber.

The optical fibers may be circular in cross-section, or they may have other shapes (i.e., square). Circular fibers are often preferred when long fiber lengths (30–100 cm) are used because they are more efficient in transmitting light quanta from the site of interaction to the photomultipliers at their end. The optical fibers used in position sensitive detectors are typically at least 20 cm long. Square fibers are preferred in a compact detector design because they fill the detector volume more fully and optical contact can be more readily achieved between two fibers at right angles.

Figure 6:
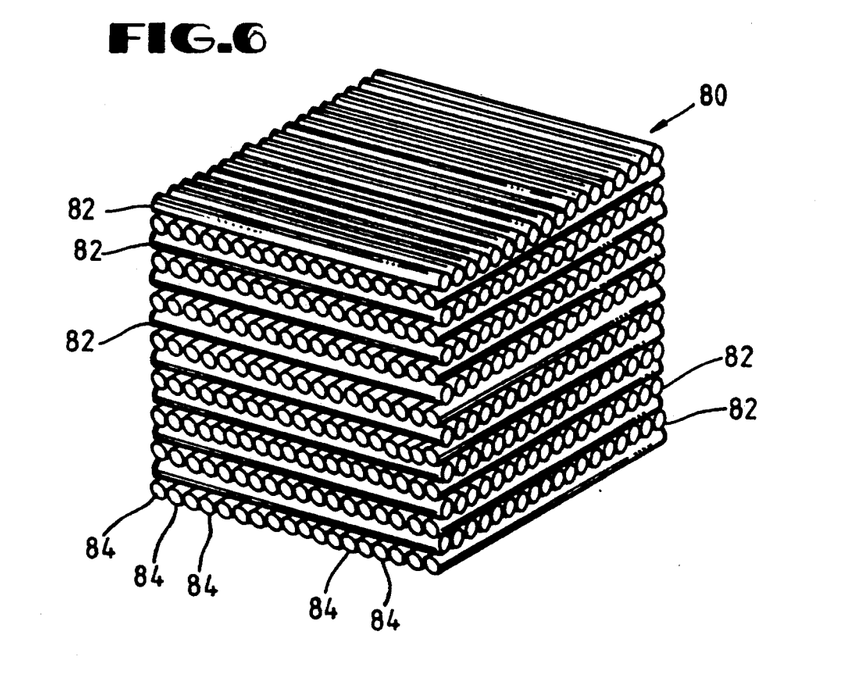
FIG. 6 shows a multi-layer array of detector fibers in accordance with the present invention.

The fibers are preferably arranged in a multi-layer array 80 as shown in FIG. 6. The array 80 is composed of parallel alternating layers 82, each of which is composed of a plurality of optical fibers 84. Alternate layers have different orientations in the X-Y plane, and preferably form an angle 60°–90°. Most preferably they are orthogonal.

At intersection points in the array 80, an optical fiber in one layer contacts a optical fiber from another, adjacent layer at a non-zero angle.

The layers of fibers may be all identical, or may be alternating layers of scintillating and non-scintillating optical fibers. The scintillating layer is the layer that reacts with the gamma ray, while the non-scintillating layer is the layer that "conferences" with (receives light from) the reacting layer.

Figure 7:
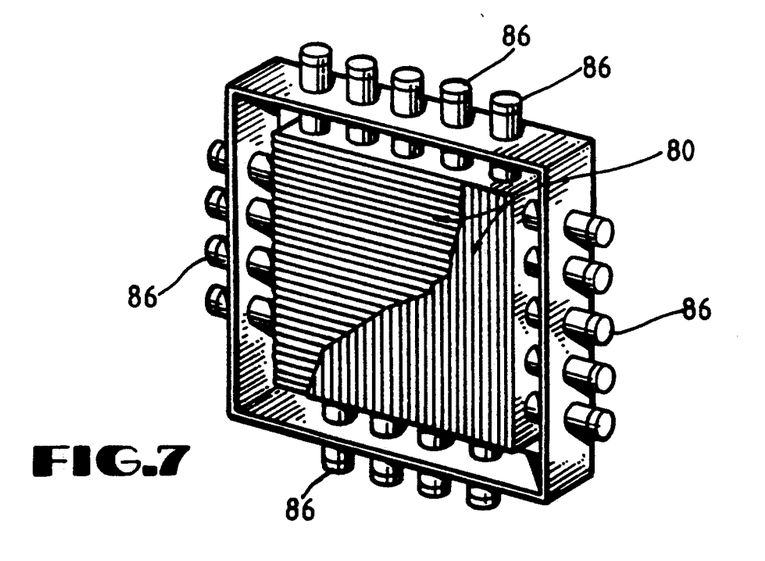
FIG. 7 shows a multi-layer array of detector fibers, coupled to a plurality of photomultipliers, in accordance with the present invention.
Figure 8A:
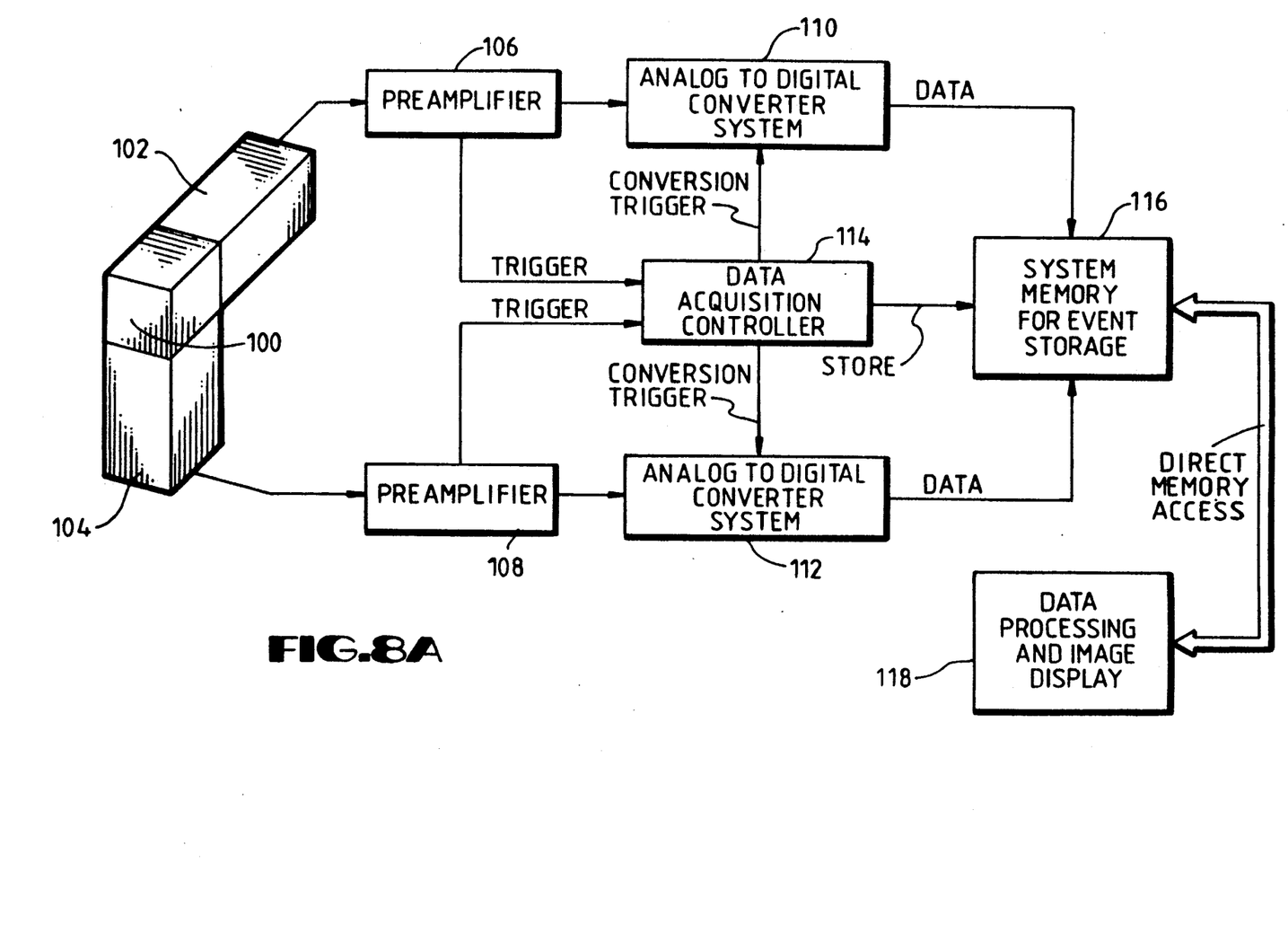
FIG. 8A shows apparatus in accordance with the present invention in block diagram form.

FIG. 7 shows an array 80 of fibers, coupled to photomultipliers 86. Suitable photomultipliers are Hamamatsu R 2486 position sensitive photomultipliers. FIG. 8A shows the entire apparatus, including electronics, in block diagram form. A fiber detector array 100 is connected to position sensitive photomultipliers 102 and 104, which are, in turn, connected to preamplifiers 106 and 108. The outputs of the preamplifiers are connected to A/D converter systems 110 and 112. The preamplifiers 106 and 108 also trigger a data acquisition controller 114, which in turn triggers the A/D conversion in systems 110 and 112. The A/D converter systems and the data acquisition controller 114 are connected to a system memory 116 for event storage. Data processing and image display apparatus 118, such as a personal computer, can directly access the system memory 116.

Figure 8B:
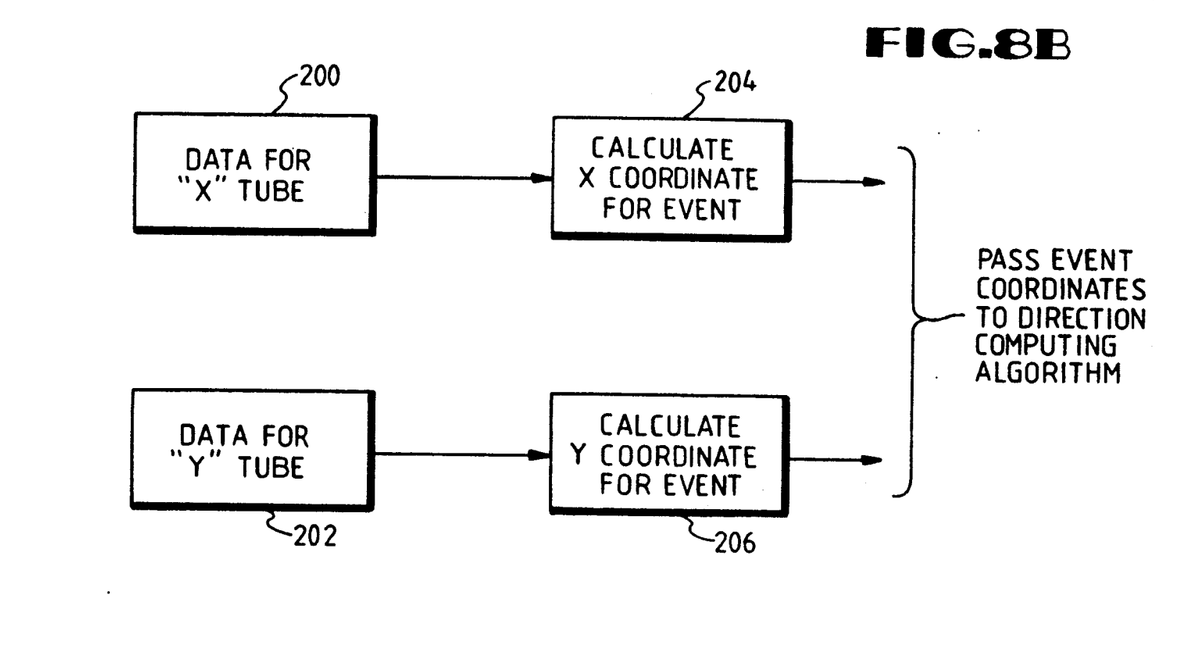
FIG. 8B shows in block diagram form the software which can be used with the apparatus of FIG. 8A.

FIG. 8B shows a block diagram of software that can be used with the apparatus of FIG. 8A. In the nomenclature of FIG. 8B, the "x tube" indicates a photomultiplier tube connected to fibers oriented in the x direction, and the "y tube" indicates the photomultiplier tube connected to fibers oriented in the y direction. Data for the x tube 200 and data for the y tube 202 are used in calculating the x, y, and z coordinates, respectively, for the event (204, 206). The x, y, and z event coordinates are then used in a direction computing algorithm to determine the site of the event and, subsequently, to store and/or display that information.

The preferred conditions for conference sensing include that the fibers in one plane should not transmit quanta of light to other fibers in the same plane. Such intraplanar transmission of light would create unwanted noise. Further, it is desirable that, for a given point on a fiber in one layer, an event at that point should result in transfer of light to a small number of fibers in the adjacent plane, most preferably to a single fiber in the adjacent plane.

Changing the angle between the fibers away from 90° does not increase efficiency and does tend to decrease resolution. Accordingly, the fibers in one plane are preferably at approximately 90° angles to the fibers in the adjacent planes.

As the number of fibers increases, uncontrolled crosstalk may increase and the signal to noise ratio may worsen. This may make it advantageous to minimize the number of fibers which are employed in the detector. Using 3 mm diameter fibers, a detector having an overall size of 10×10×5 cm could be constructed with only 578 fibers, in 17 layers of 34 fibers each. In contrast, 20,000 fibers may be needed in prior art detecting systems when 0.5 mm diameter fibers are employed. It is expected that a 3 mm fiber size would result in a 1.5 mm resolution at the object imaged, as this lies approximately halfway between the detectors. Thus, the object resolution coincides with the intrinsic positron smearing range of >1 mm. (Note that prior art systems use ≈4–7 mm resolution )

Other possible variations in embodiments of the present invention are as follows:

Detector fibers could be made using a cladding with a constant index of refraction and a constant concentration of waveshifter. Alternatively, the index of refraction could be smoothly varied across the core-cladding interface, instead of having a step change. Fibers having a cladding with a graded index of refraction could have either a constant concentration of waveshifter or a graded concentration of waveshifter in the cladding. Likewise, fibers having a cladding with a constant index of refraction could have either a graded or stepped concentration of waveshifter in the cladding. Another possible variation would be to use a stepped concentration of the waveshifter in which the inner part of the cladding had no waveshifter. Thus, no waveshifting would occur until the ray had penetrated to the outer part of the cladding. This design could be used to suppress waveshifting of the evanescent wave penetration associated with total internal reflection by making the thickness of the waveshifter-free cladding commensurate with the penetration depth of the evanescent wave.

The relative indices of refraction for the core and the cladding will determine the conversion efficiency, since large values for $\theta_c$ will permit a larger percentage of the primary scintillation light to interact with the core. Conversely, small values of $\theta_c$ will increase the fraction of the waveshifted light which will propagate down the fiber. Thus, there may be an optimal value for the ratio of the indices of refraction for the core and the cladding.

Light detectors with specified spectral responses could be used to view only that light originating in the fiber or that light originating in the cladding. Other schemes might be used, for example having one photodetector sensitive to only one emission of radiation and the other being sensitive to both emissions. These schemes would allow identification of the fiber in which the original scintillation occurred, thus increasing the spatial resolution of the radiation detector.

The preceding description is intended to illustrate certain embodiments of the present invention. It is not intended to be an exhaustive list of all possible embodiments. Those skilled in this field will recognize that modifications could be made which would remain within the scope of the invention.

We claim:

1. Apparatus for detecting and locating the origin of radiation in a medical diagnostic imaging system, including:
    at least one primary optical fiber which has a scintillating core surrounded by cladding, where the cladding has at least one waveshifter incorporated in it, with the at least one primary fiber being positioned to receive radiation from a radiation source;
    at least one secondary optical fiber which intersects the primary fiber at a non-zero angle and which has a core surrounded by cladding, and whose cladding is in optical contact with the cladding of the at least one primary fiber;
    a plurality of means for detecting light which are coupled to the at least one primary fiber and the at least one secondary fiber; and
    means for collecting and processing data from the means for detecting light, to locate the origin of the radiation.

2. The apparatus of claim 1, wherein the apparatus includes a plurality of primary fibers and a plurality of secondary fibers, where the primary fibers are arranged substantially parallel to each other in a first plane, and where the secondary fibers are arranged substantially parallel to each other in a second plane which is parallel and adjacent to the first plane.

3. The apparatus of claim 2, where the primary fibers are orthogonal to the secondary fibers.

4. The apparatus of claim 2, where the cladding of each secondary fiber is in optical contact with the cladding of at least one primary fiber at a point where that secondary fiber intersects that at least one primary fiber.

5. The apparatus of claim 2, where the primary fibers and the secondary fibers are arranged in concentric, curved layers.

6. The apparatus of claim 1, where the at least one secondary fiber is nonscintillating.

7. Apparatus for detecting and locating the origin of a radiation in a medical diagnostic imaging system, including:
    an array of optical fibers which includes a plurality of layers which are located in parallel planes that are adjacent one to the next, where (a) each layer includes a plurality of substantially parallel optical fibers that from angle between 60°–90° with the fibers in the layer immediately above and to the fibers in the layer immediately below, (b) each fiber has a core surrounded by cladding, (c) the fibers in at least one layer have scintillating cores and at least one waveshifter incorporated in their cladding, (d) the cladding of each fiber is in optical contact with the cladding of at least one fiber in an adjacent layer, and (e) the array of fibers is positioned to receive radiation from a radiation source;
    a plurality of position sensitive photomultipliers coupled to the fibers in the array for detecting light generated in the fibers; and
    means for collecting and processing data from the position sensitive photomultipliers to locate the origin of the radiation.

8. A method for detecting and locating the origin of radiation in a patient as part of a medical diagnostic imaging system, including the steps of:
    emitting radiation from a radiation source in a patient's body;
    ejecting an electron in the scintillating core of a primary optical fiber as a result of an interaction between the radiation and the scintillating core of the fiber, thereby causing the emission of light quanta in the primary fiber;
    transferring a portion of the light quanta from the primary fiber to a secondary optical fiber which intersects the primary fiber at a non-zero angle and is in optical contact with the primary fiber, by means of re-emission of the light quanta when they interact with cladding that surrounds the primary fiber, the cladding surrounding the primary fiber incorporating at least one waveshifter, resulting in waveshifting of the light when it is re-emitted;
    detecting the light quanta from the primary fiber and the secondary fiber; and p1 determining the location of the interaction between the radiation and the primary fiber by identifying the location of the contact between the primary fiber and the secondary fiber.

9. A method for detecting and locating the origin of radiation in a patient as part of a medical diagnostic imaging system, including the steps of:

(a) emitting radiation from a radiation source in a patient's body;

(b) ejecting an electron in the scintillating core of a primary optical fiber, which is part of a layer of substantially parallel primary optical fibers located in a first plane, as a result of an interaction between the radiation and the scintillating core of the primary fiber, thereby causing the emission of light quanta in the primary fiber;

(c) transferring a portion of the light quanta from the primary fiber to a secondary optical fiber, which is in optical contact with the primary fiber, and which is part of a layer of substantially parallel secondary optical fibers that from a nonzero angle with the primary fibers and are located in a second plane that is parallel to the first plane, by means for re-emission of the light quanta when they interact with cladding that surrounds the primary fiber, the cladding surrounding the primary fiber incorporating at least one waveshifter, resulting in waveshifting of the light when it is re-emitted.

(d) detecting which fibers in the layer of primary fibers and which fibers in the layer of secondary fibers propagate light quanta at substantially the same time; and (e) determining the location of the interaction between the radiation and the primary fiber by identifying the location of the contact between the primary fiber which propagated light and the secondary fiber which propagated light at substantially the same time.

10. The method of claim 9, further comprising the steps of:

(f) emitting a second radiation from the radiation source in the patient's body at substantially the same time as the radiation of step (a) is emitted, with the second radiation being emitted in the opposite direction from the radiation of step (a);

(d) ejecting a second electron in the scintillating core of a primary optical fiber, which is separate from the primary fiber of step (b) and which is located on the opposite side of the patient's body from the primary fiber of step (b), and which is part of a layer of substantially parallel primary optical fibers located in a third plane, as a result of an interaction between the radiation of step (f) and the scintillating core of the primary fiber, thereby causing the emission of light quanta in the primary fiber;

(h) transferring a portion of the light quanta of step (g), from the primary fiber of step (g) to a secondary optical fiber, which is separate from the secondary fiber of step (c), and which is in contact with the primary fiber of step (g), and which is part of a layer of substantially parallel optical fibers that form a non-zero angle with the primary fibers of step (g) and are located in a fourth plane that is parallel to the third plane, by means of re-emission of the light quanta when they interact with cladding that surrounds the primary fiber of step (g), the cladding surrounding the primary fiber of step (g) incorporating at least one waveshifter, resulting in waveshifting of the light when it is re-emitted;

(i) detecting which fibers in the layer of primary fibers of step (g) and which fibers in the layer of secondary fibers of step (h) propagate light quanta at substantially the same time; and (j) determining the location of the interaction between the second radiation and the primary fiber of step (g) by identifying the location of the contact between the primary fiber which propagated light and the secondary fiber which propagated light at substantially the same time.

11. The method of claim 9, further comprising the steps of:

(f) measuring the intensity of the light produced in the primary fiber of step (b);

(g) ejecting a second electron in the scintillating core of a primary optical fiber at substantially the same time at which the electron of step (b) is ejected, which primary fiber is separate from the primary fiber of step (b) and which is located on the same side of the patient's body as the primary fiber of step (b), and which primary fiber is part of a layer of substantially parallel primary optical fibers located in a third plane, as a result of an interaction between the same radiation of step (a) and the scintillating core of the primary fiber, thereby causing the emission of light quanta in the primary fiber;

(h) transferring a portion of the light quanta from the primary fiber of step (g) to a secondary optical fiber, which is in contact with the primary fiber of step (g), and which secondary fiber is separate from the secondary fiber of step (c) and is part of a layer of substantially parallel fibers that form a non-zero angle with the primary fibers and are located in a fourth plane that is parallel to the third plane, by means of re-emission of the light quanta when they interact with cladding that surrounds the primary fiber of step (g), the cladding surrounding the primary fiber of step (g), incorporating at least one waveshifter, resulting in waveshifting of the light when it is re-emitted;

(i) detecting which fibers in the layer of primary fibers of step (b) and which fibers in the layer of secondary fibers of step (h) propagate light quanta at substantially the same time;

(j) determining the location of the interaction between the radiation and the primary fiber of step (g) by identifying the location of the contact between the primary fiber which propagated light and the secondary fiber which propagated light at substantially the same time; and (k) determining the direction of the radiation emitted in the patient's body by determining the line joining the location of step (e) and the location of step (j), and determining the electron energy corresponding to the light intensity of step (f).

* * * * *